United States Patent
Solomon

(10) Patent No.: US 10,092,380 B1
(45) Date of Patent: Oct. 9, 2018

(54) MANUALLY-OPERATED TOOTH-BUFFING TOOL

(71) Applicant: Justin Solomon, Diamond Bar, CA (US)

(72) Inventor: Justin Solomon, Diamond Bar, CA (US)

(*) Notice: Subject to any disclaimer, the term of this patent is extended or adjusted under 35 U.S.C. 154(b) by 129 days.

(21) Appl. No.: 15/162,945

(22) Filed: May 24, 2016

(51) Int. Cl.
*A61C 17/00* (2006.01)
*B24D 15/02* (2006.01)

(52) U.S. Cl.
CPC ............ *A61C 17/005* (2013.01); *B24D 15/02* (2013.01)

(58) Field of Classification Search
CPC ....... A45B 5/00; A45B 17/08; A45B 2200/10; A45B 2200/30; A61C 3/00; A61C 12/005; A61C 12/222; B24D 15/00; B24D 15/02; B24D 15/023; B24D 15/04; Y10T 29/4561; Y10T 29/4567; Y10T 29/4594
See application file for complete search history.

(56) References Cited

U.S. PATENT DOCUMENTS

| | | | | | |
|---|---|---|---|---|---|
| 1,427,503 A | * | 8/1922 | Wake | ........................ | A61C 3/06 132/76.4 |
| 2,719,315 A | * | 10/1955 | Sheehan | ................... | A46B 7/04 15/167.1 |
| 3,010,131 A | * | 11/1961 | Kisky | ...................... | A46B 9/04 15/143.1 |
| 3,590,414 A | * | 7/1971 | Gores | ....................... | A46B 7/04 128/DIG. 15 |
| 4,083,078 A | * | 4/1978 | Shimizu | .................. | A46B 3/005 15/244.1 |
| 4,628,564 A | * | 12/1986 | Youssef | .................. | A46B 9/005 15/110 |
| 4,638,521 A | * | 1/1987 | Potente | ................... | A46B 9/005 15/117 |
| 5,273,425 A | * | 12/1993 | Hoagland | ................. | A46B 5/02 433/1 |
| 5,766,193 A | * | 6/1998 | Millner | ................. | A61B 17/244 606/161 |
| 5,799,355 A | | 9/1998 | Burch | | |
| 6,083,235 A | * | 7/2000 | Wagner | ................ | A61B 17/244 606/161 |
| 6,205,611 B1 | * | 3/2001 | Vigil | ........................ | A46B 7/04 132/308 |
| D465,847 S | * | 11/2002 | Jacobs | ............... | A46B 15/0081 D24/147 |
| 6,503,082 B1 | | 1/2003 | Takahashi | | |
| 7,712,175 B2 | | 5/2010 | Blanchard | | |
| D619,717 S | | 7/2010 | Toshima | | |
| D638,628 S | * | 5/2011 | Nanda | .......................... | D24/147 |
| 2003/0167582 A1 | * | 9/2003 | Fischer | ................ | A61B 17/244 15/22.1 |

(Continued)

FOREIGN PATENT DOCUMENTS

WO 0121036 A1 3/2001

*Primary Examiner* — Timothy V Eley

(57) ABSTRACT

The manually-operated tooth-buffing tool is a dental appliance that is adapted for use with a tooth. The manually-operated tooth-buffing tool is a handheld disposable tool that is used for the buffing and polishing of the tooth. The manually-operated tooth-buffing tool comprises a buffing head and a handle. The buffing head further comprises a grit that is rubbed against the tooth such that the plaque, calculus, and stains on the tooth are removed and the surface of the tooth is smooth.

9 Claims, 3 Drawing Sheets

(56) References Cited

U.S. PATENT DOCUMENTS

| | | |
|---|---|---|
| 2006/0027246 A1 | 2/2006 | Wilkinson |
| 2007/0265555 A1* | 11/2007 | Deng ................... A61H 13/00 601/141 |
| 2011/0116858 A1 | 5/2011 | Burrowes |
| 2012/0110767 A1 | 5/2012 | Newham |
| 2012/0258418 A1 | 10/2012 | Shen |
| 2014/0082866 A1* | 3/2014 | Fischer ............... A46D 1/0284 15/22.1 |
| 2017/0281323 A1* | 10/2017 | Fischer ............... A46D 1/0284 |

* cited by examiner

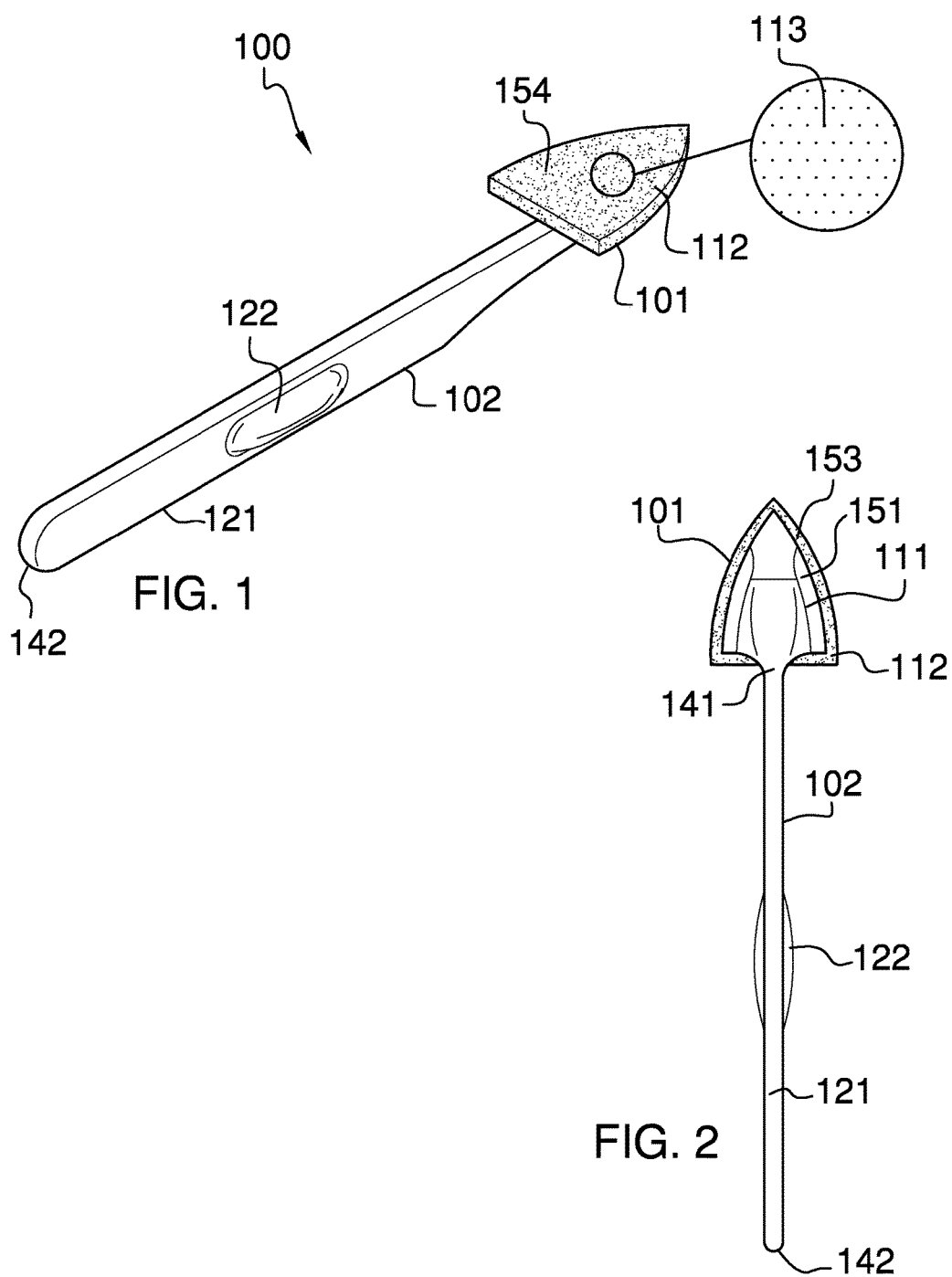

MANUALLY-OPERATED TOOTH-BUFFING TOOL

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of tools for grinding, buffing, or polishing, more specifically, a manual polishing tool adapted for use on teeth.

SUMMARY OF INVENTION

The manually-operated tooth-buffing tool is a dental appliance that is adapted for use with a tooth. The manually-operated tooth-buffing tool is a handheld disposable tool that is used for the buffing and polishing of the tooth. The manually-operated tooth-buffing tool comprises a buffing head and a handle. The buffing head further comprises a grit that is rubbed against the tooth such that the plaque, calculus, and stains on the tooth are removed and the surface of the tooth is smooth. The creation of the smooth tooth surface inhibits the future accretion of plaque, calculus, and stains.

These together with additional objects, features and advantages of the manually-operated tooth-buffing tool will be readily apparent to those of ordinary skill in the art upon reading the following detailed description of the presently preferred, but nonetheless illustrative, embodiments when taken in conjunction with the accompanying drawings.

In this respect, before explaining the current embodiments of the manually-operated tooth-buffing tool in detail, it is to be understood that the manually-operated tooth-buffing tool is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the manually-operated tooth-buffing tool.

It is therefore important that the claims be regarded as including such equivalent construction insofar as they do not depart from the spirit and scope of the manually-operated tooth-buffing tool. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

FIG. 1 is a perspective view of an embodiment of the disclosure.

FIG. 2 is a back view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 3:
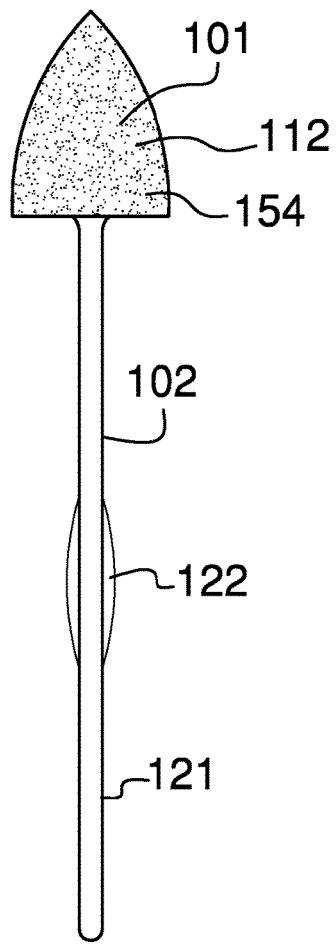
FIG. 3 is a front view of an embodiment of the disclosure.
Figure 4:
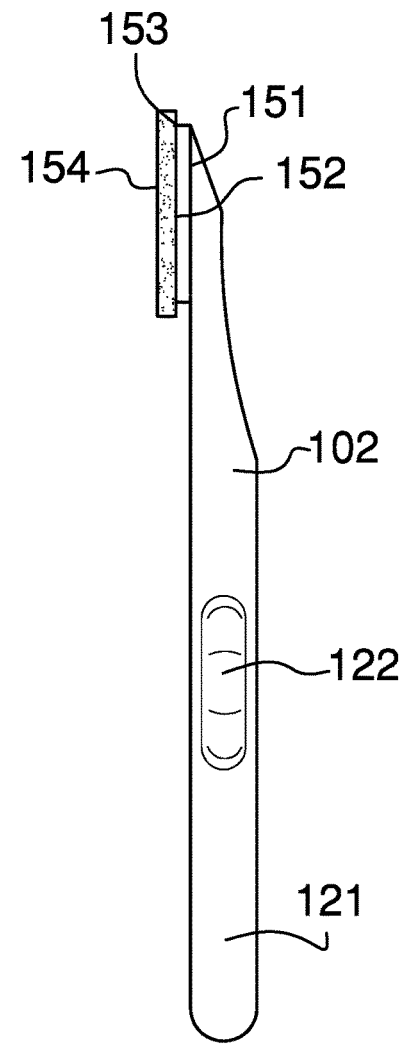
FIG. 4 is a side view of an embodiment of the disclosure.
Figure 5:
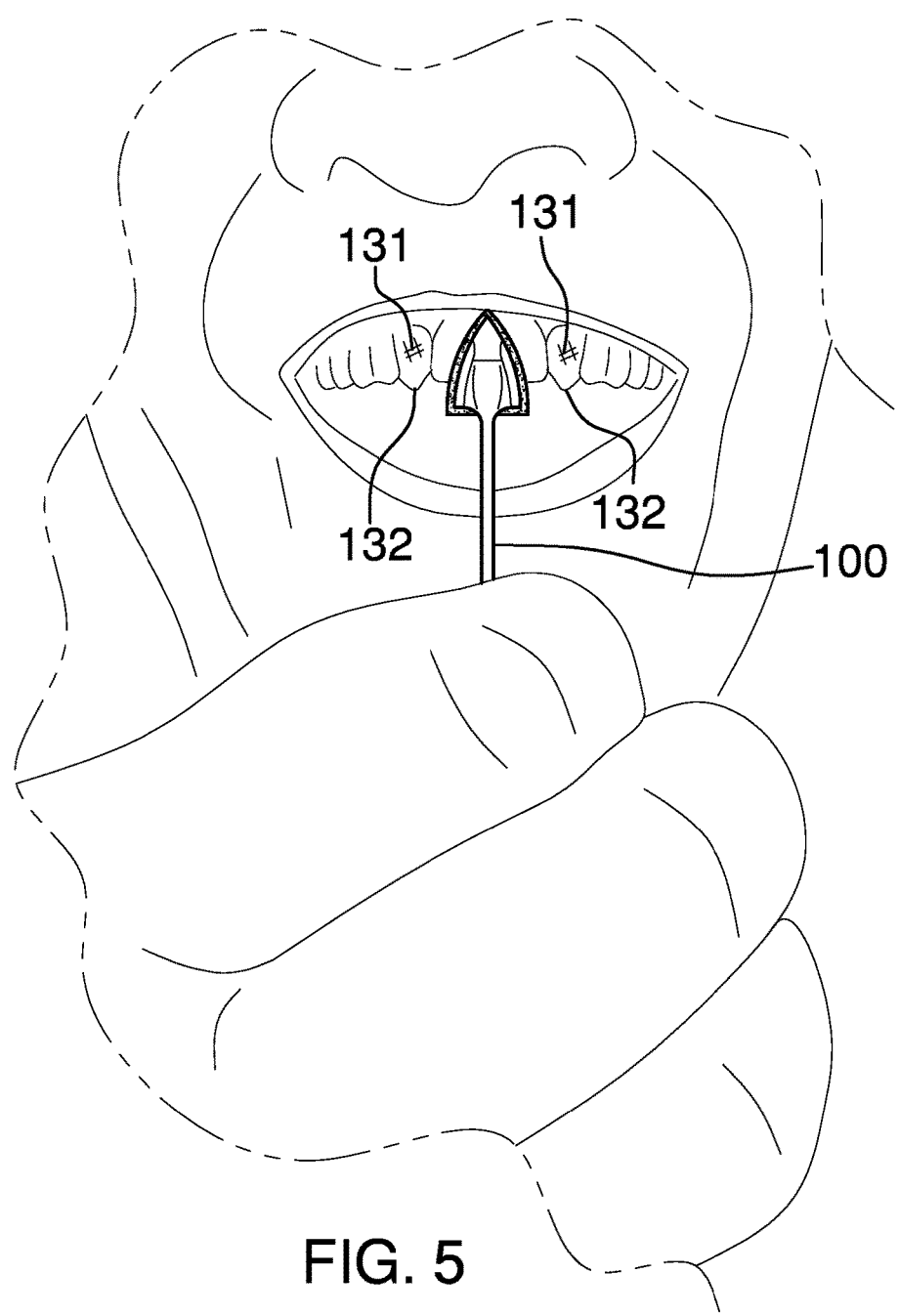
FIG. 5 is an in use view of an embodiment of the disclosure.

Detailed reference will now be made to one or more potential embodiments of the disclosure, which are illustrated in FIGS. 1 through 5.

The manually-operated tooth-buffing tool 100 (hereinafter invention) comprises a buffing head 101 and a handle 102. The invention 100 is a dental appliance that is adapted for use with a tooth 132. The invention 100 is a handheld disposable tool that is used for the buffing and polishing of the tooth 132. The invention 100 is manually powered. The buffing head 101 further comprises a grit 113 that is rubbed against the tooth 132 such that such that the plaque, calculus, and stains (hereinafter detritus 131) on the tooth 132 are removed and the surface of the tooth 132 is left smooth. The creation of the smooth tooth 132 surface inhibits the future accretion of detritus 131.

The buffing head 101 comprises a buffing plate 111, a buffing substrate 112, and the grit 113. As shown most clearly in FIGS. 2 and 3, the buffing plate 111 is a rigid structure that is formed in the shape of an oblique spherical triangle. The buffing plate 111 is further defined with a first surface 151 and a second surface 152. The buffing substrate 112 is a structure that is formed from an elastomeric material that deforms when force is applied to the surface of the buffing substrate 112. The buffing substrate 112 is further defined with a third surface 153 and a fourth surface 154. As shown most clearly in FIG. 2 the buffing substrate 112 is formed in the shape of an oblique spherical triangle. The span of perimeter of the buffing substrate 112 is greater than the span of the perimeter of the buffing plate 111 such that when the buffing substrate 112 is attached to the buffing plate 111, the buffing plate 111 is not visible when the buffing substrate 112 is viewed head on. The fourth surface 154 of the buffing substrate 112 has the grit 113 attached to it. The third surface 153 of the buffing substrate 112 is attached to the second surface 152 of the buffing plate 111.

The grit 113 is a substance made of a plurality of particulates. Each of the plurality of particulates is a particle that acts as an abrasive agent when the particle is rubbed against a tooth 132. The combined rubbing action of all the particles contained within the plurality of particulates work like sandpaper to: 1) remove detritus 131 from the tooth 132; and, 2) create the desired smooth surface on the tooth 132. Abrasive agents suitable for use as grit 113 include, but are not limited to, boron, silicon carbide, garnet, emery, zirconium silicate, zirconium oxide, pumice, perlite, aluminum oxide, and calcium carbonate. If a hard abrasive is desired in the grit 113, the use of boron or silicon carbide is recommended. If a softer abrasive is desired in the grit 113, the use of aluminum oxide or calcium carbonate is recommended.

The handle 102 comprises a shaft 121 and a grip 122. The shaft 121 further comprises a first end 141 and a second end 142. The shaft 121 is a long and narrow structure that is roughly cylindrical in shape. The shaft 121 is held in the hand of a user. The first surface 151 of the buffing plate 111 is attached to the first end 141 of the shaft 121 such that the face of the buffing plate 111 is parallel to the center axis of the handle 102. As shown most clearly on FIG. 2, the grip 122 is one or more structures that are attached to the shaft 121. The grip 122 provides a purchase allowing the shaft 121 to be more securely held during use.

To use the invention 100, the invention 100 is grasped via the handle 102 and the buffing head 101 is placed in the mouth such that the buffing substrate 112 and the grit 113 are in contact with a tooth 132. The handle 102 is then moved such that the buffing substrate 112 and the grit 113 are rubbed against the tooth 132. In instances where substantial plaque, calculus, and stain has accumulated on the tooth 132 a plurality of instantiations of the invention 100 may be required. Specifically, each of the plurality of instantiations of the invention 100 will be differentiated by the particle size of the grit 113 applied to the buffing head 101. The instantiation of the invention 100 formed with the grit 113 containing the largest particles is first used to buff the tooth 132. Instantiations of the invention 100 formed with grit 113 of sequentially smaller particles are then used until all plaque, calculus, and stain has been appropriately removed.

In the first potential embodiment of the disclosure, the buffing plate 111, the shaft 121 and the grip 122 are formed as a single unit from molded plastic. The buffing substrate 112 is formed from a polyurethane. The buffing substrate 112 is attached to the buffing plate 111 using a first adhesive. The grit 113 is attached to the fourth surface 154 of the buffing substrate 112 with a second adhesive formed from vegetable starch. The first potential embodiment of the disclosure, is disposed of after its intended over the entire dentition of the user.

A second potential embodiment of the disclosure is identical to the first potential embodiment of the disclosure with the addition that the grit 113 is made from calcium carbonate. A third potential embodiment of the disclosure is identical to the first potential embodiment of the disclosure with the addition that the grit 113 is made from boron. A fourth potential embodiment of the disclosure is identical to the first potential embodiment of the disclosure with the addition that the grit 113 is treated with a fluoride. Methods to infuse tooth treatments with fluoride are well known and documented in the dental arts.

The following definitions were used in this disclosure:

Adhesive: As used in this disclosure, an adhesive is a chemical substance that can be used to adhere two or more objects to each other. Types of adhesives include, but are not limited to, epoxies, polyurethanes, polyimides, or cyanoacrylates, silicone, or latex based adhesives.

Center Axis: As used in this disclosure, the center axis is the axis of a cylinder or cone like structure. When the center axes of two-cylinder or like structures share the same line they are said to be aligned. When the center axes of two-cylinder like structures do not share the same line they are said to be offset.

Detritus: As used in this disclosure, detritus refers to plaque, calculus, and stains that accretes on a tooth.

Elastic: As used in this disclosure, an elastic is a material or object that deforms when a force is applied to it and that is able to return to its original shape after the force is removed. A material that exhibits these qualities is also referred to as an elastomeric material.

Perimeter: As used in this disclosure, a perimeter is one or more curved or straight lines that bounds an enclosed area on a plane or surface. The perimeter of a circle is commonly referred to as a circumference.

Spherical Triangle: As used in this disclosure, a spherical triangle is a figure with three vertices that is formed on the surface of the sphere. The three vertices of the spherical triangle are formed from the intersection of three great circular arcs that are drawn through the sphere.

Oblique Spherical Triangle: As used in this disclosure, an oblique spherical triangle is a spherical triangle in which: 1) no angle of the oblique spherical triangle is greater than 90 degrees; and, 2) no more than two angles of the oblique spherical triangle equal 90 degrees. Technical note: An oblique spherical triangle with only one angle equal to 90 degrees is considered an oblique spherical triangle but is commonly referred to as a right spherical triangle.

With respect to the above description, it is to be realized that the optimum dimensional relationship for the various components of the invention described above and in FIGS. 1 through 5, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A polishing tool comprising:
a buffing head and a handle;
wherein the polishing tool is adapted for use with a tooth;
wherein the polishing tool is a dental appliance;
wherein the polishing tool is handheld;
wherein the polishing tool is manually powered;
wherein the polishing tool is disposable;
wherein the polishing tool is adapted to buff and polish the tooth;
wherein the buffing head comprises a buffing plate, a buffing substrate, and a grit;
wherein the grit is attached to the buffing substrate;
wherein the buffing substrate is attached to the buffing plate;
wherein the buffing plate is further defined with a first surface and a second surface;

wherein the buffing substrate is further defined with a third surface and a fourth surface;
wherein the buffing plate is a rigid structure that is formed in the shape of a triangle;
wherein each side of said triangle has a curvature;
wherein the buffing substrate is a structure that is formed from an elastomeric material;
wherein the buffing substrate is larger than the buffing plate;
wherein the fourth surface of the buffing substrate has the grit attached thereon;
wherein the third surface of the buffing substrate is attached to the second surface of the buffing plate;
wherein the grit is a substance made of a plurality of particulates;
wherein each of the plurality of particulates is a particle that acts as an abrasive agent when the particle is rubbed against a tooth;
wherein the handle comprises a shaft;
wherein the shaft is further defined with a first end and a second end;
wherein the first surface of the buffing plate is attached to the first end of the shaft;
wherein the buffing plate and the shaft are formed as a single unit.

2. The polishing tool according to claim 1 wherein the grit is formed from a substance that is selected from the group consisting of boron, silicon carbide, garnet, emery, zirconium silicate, zirconium oxide, pumice, perlite, aluminum oxide, and calcium carbonate.

3. The polishing tool according to claim 1 wherein the buffing substrate is attached to the buffing plate using a first adhesive.

4. The polishing tool according to claim 3 wherein the grit is attached to the fourth surface of the buffing substrate with a second adhesive.

5. The polishing tool according to claim 4 wherein the grit comprises calcium carbonate.

6. The polishing tool according to claim 5
wherein the buffing substrate is formed from a polyurethane;
wherein the second adhesive is a starch based adhesive.

7. The polishing tool according to claim 4 wherein the grit comprises boron.

8. The polishing tool according to claim 7
wherein the buffing substrate is formed from a polyurethane;
wherein the second adhesive is a starch based adhesive.

9. The polishing tool according to claim 4 wherein the grit is treated with fluoride.

* * * * *